(12) United States Patent
Matev et al.

(10) Patent No.: US 10,273,448 B2
(45) Date of Patent: Apr. 30, 2019

(54) MEDIUM CONTAINING URIDINE AND N-ACETYL-D-MANNOSAMINE

(71) Applicant: JCR Pharmaceuticals Co., Ltd., Ashiya-shi (JP)

(72) Inventors: Miroslav Matev, Kobe (JP); Kenichi Takahashi, Kobe (JP); Shinji Kakimoto, Kobe (JP); Ayaka Kotani, Kobe (JP)

(73) Assignee: JCR PHARMACEUTICALS CO., LTD., Ashiya-shi (JP)

( * ) Notice: Subject to any disclaimer, the term of this patent is extended or adjusted under 35 U.S.C. 154(b) by 294 days.

(21) Appl. No.: 15/365,331

(22) Filed: Nov. 30, 2016

(65) Prior Publication Data
US 2017/0073633 A1  Mar. 16, 2017

Related U.S. Application Data

(63) Continuation of application No. PCT/JP2015/066123, filed on May 27, 2015.

(30) Foreign Application Priority Data

May 31, 2014 (JP) ................. 2014-124742

(51) Int. Cl.
| | | |
|---|---|---|
| C12N 5/00 | (2006.01) | |
| C12P 21/00 | (2006.01) | |
| C07K 14/505 | (2006.01) | |
| C12N 15/09 | (2006.01) | |
| C12P 21/02 | (2006.01) | |

(52) U.S. Cl.
CPC .......... C12N 5/0018 (2013.01); C07K 14/505 (2013.01); C12N 15/09 (2013.01); C12P 21/005 (2013.01); C12P 21/02 (2013.01); *C12N 2500/32* (2013.01); *C12N 2500/34* (2013.01); *C12N 2500/40* (2013.01)

(58) Field of Classification Search
None
See application file for complete search history.

(56) References Cited

U.S. PATENT DOCUMENTS

| | | | |
|---|---|---|---|
| 5,705,364 A | 1/1998 | Etcheverry et al. | |
| 6,391,633 B1 | 5/2002 | Stern et al. | |
| 6,395,484 B1 | 5/2002 | Brandt et al. | |
| 6,544,748 B2 | 4/2003 | Stern et al. | |
| 6,548,296 B1 | 4/2003 | Stern et al. | |
| 6,555,373 B1 | 4/2003 | Stern et al. | |
| 6,673,575 B1 | 1/2004 | Franze et al. | |
| 6,846,673 B2 | 1/2005 | Brandt et al. | |
| 7,186,529 B2 | 3/2007 | Stern et al. | |
| 7,214,514 B2 | 5/2007 | Brandt et al. | |
| 7,214,532 B2 | 5/2007 | Stern et al. | |
| 7,541,164 B2 | 6/2009 | Schilling et al. | |
| 7,659,373 B2 | 2/2010 | Burg et al. | |
| 8,609,370 B2 | 12/2013 | Goletz et al. | |
| 2012/0015438 A1 | 1/2012 | Schilling et al. | |

FOREIGN PATENT DOCUMENTS

| | | |
|---|---|---|
| CN | 101657535 A | 2/2010 |
| JP | 05-71934 A | 3/1993 |
| JP | 08-027181 A | 1/1996 |
| JP | 11-507523 A | 7/1999 |
| JP | 2001-525342 A | 12/2001 |
| JP | 2006-520186 A | 9/2006 |
| JP | 2007-522179 A | 8/2007 |
| WO | 2008/015418 A2 | 2/2008 |
| WO | WO 2009/127826 A1 | 10/2009 |

OTHER PUBLICATIONS

Baker et al. (Metabolic control of recombinant protein N-glycan processing in NS0 and CHO cells, Biotechnol Bioeng., May 5, 2001; 73(3): 188-202).*

Niki et al., "An Investigation of Intracellular Glycosylation Activities in CHO Cells: Effects of Nucleotide Sugar Precursor Feeding", Biotechnology and Bioengineering, vol. 107, No. 2, 2010, pp. 321-336.

"GlutaMAX I (100X)" Product manual, Form No. 3960, 2010, 1 page.

Pels Rijcken, et al., "The effect of increasing nucleotide-sugar concentrations on the incorporation of sugars into glycoconjugates in rat hepatocytes", Biochem J., vol. 305, 1995, pp. 865-870.

Office Action dated Nov. 26, 2018 in Chinese Patent Application No. 201580029017.2.

* cited by examiner

Primary Examiner — Suzanne M Noakes
Assistant Examiner — Jae W Lee
(74) Attorney, Agent, or Firm — Oblon, McClelland, Maier & Neustadt, L.L.P.

(57) ABSTRACT

Provided are a novel medium for expressing glycoproteins by culturing cells and a method for producing glycoproteins by culturing cells in the medium. Further provided are a medium comprising uridine and N-acetyl-D-mannosamine for the use of expression of a glycoprotein by culturing cells and a method for producing glycoproteins by culturing cells in the medium.

25 Claims, 6 Drawing Sheets

Specification includes a Sequence Listing.

MEDIUM CONTAINING URIDINE AND N-ACETYL-D-MANNOSAMINE

CROSS-REFERENCE TO RELATED APPLICATIONS

The present application is a continuation of International Application No. PCT/JP2015/066123, filed May 27, 2015, which is based upon and claims the benefits of priority to Japanese Application No. 2014-124742, filed May 31, 2014. The entire contents of these applications are incorporated herein by reference.

BACKGROUND OF THE INVENTION

Field of the Invention

The present invention relates to a cell culture medium containing uridine and N-acetyl-D-mannosamine, and a method for production of a glycoprotein comprising culturing cells transformed by an exogenous DNA encoding the glycoprotein by using the cell culture medium.

Discussion of the Background

As a predominant mode of linkage between a protein and a glycan in a glycoprotein, there are N-glycosidic bond where N-acetyl-D-glucosamine is covalently linked to the asparagine residue composing the protein (N-linked glycan, N-glycoside-linked sugar chain), and O-glycosidic bond where N-acetyl-D-galactosamine is covalently linked to the serine or the threonine residue composing the protein (O-linked glycan, O-glycoside-linked sugar chain)

In mammalian cells, N-glycosidic bond-linked sugar chains of glycoproteins are those attached to asparagine residues of the proteins, through a complex pathway involving various enzymes, while the proteins, after translated from RNA, are transferred through the lumen of an endoplasmic reticulum to Golgi bodies. The major types of N-glycosidic bond-linked sugar chains are complex-type sugar chains and high mannose-type sugar chains. Complex-type sugar chains, while there are various types of them, are characterized in that their non-reducing ends consist of sialic acid residues. An example of them is shown in structural formula 2 below.

[Chem. 1]

structural formula 1

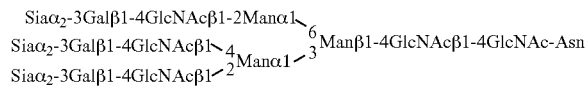

If mammalian cells, such as Chinese hamster ovary cells (CHO cells), are used in producing a recombinant glycoprotein, a large part of the sugar chains of the protein thus obtained will be a complex-type in their structure, and sialic acid residues thus will occur at the non-reducing ends of the sugar chains of such a recombinant glycoprotein. It is known that stability in the blood of a recombinant protein administered to a body is increased if complex-type sugar chains, which have sialic acid residues at their non-reducing ends, are attached to the protein (cf. Patent Document 1). Thus, when recombinant glycoproteins are to be produced which exhibit their effects while circulating in the blood, production methods using CHO cells are utilized, with which sugar chains are produced having sialic acid residues at their non-reducing ends, expecting elongation of their half-lives in the blood, and thereby augmentation of their pharmacological effects. Erythropoietin and follicle-stimulating hormone (FSH) are typical examples of such recombinant glycoproteins (cf. Patent Documents 2 and 3).

And as a half-life of a glycoprotein in blood is expected to be prolonged when more sialic residues are added to sugar chain of the glycoprotein, several methods are reported objective of which is to added more sialic residues to the glycoprotein. For example, a method is reported for the production of a recombinant glycoprotein by using host cells transformed with sialyltransferase having ability to add a sialic acid to the end of sugar chains (cf. Patent Document 4). Further, reported is that a recombinant glycoprotein added with more sialic acid residues are to be obtained by culturing mammalian cells transformed with a gene encoding a glycoprotein with the temperature lowered in a stepwise manner (cf. Patent Document 5).

Further several cell culture mediums are reported which are to be used for adding more sialic acids to a sugar chain of a glycoprotein. For example, reported is that the molar ratio of sialic acids to a recombinant glycoprotein expressed by cells can be adjusted by adding alkanoic acid such as butylic acid or the salt thereof at a predetermined concentration when the cells cultured (cf. Patent Document 6). And it has been reported that a recombinant glycoprotein having a specific degree of sialylation can be produced by adding a precursor of sialic acid such as ManNAc, acetyl-ManNAc, peracetyl-ManNAc, or fetuin to a medium (cf. Patent Document 7). And it has been reported that sialylation level of a recombinant glycoprotein can be increased by adding monosaccharides, for example, in the combination of glucose, mannose, and galactose, to a medium (cf. Patent Document 8).

PRIOR ART DOCUMENTS

Patent Documents

[Patent Document 1] JP H08-027181
[Patent Document 2] JP 2001-525342
[Patent Document 3] WO2009/127826
[Patent Document 4] JP H05-071934
[Patent Document 5] JP 2006-520186
[Patent Document 6] JP H11-507523
[Patent Document 7] JP 2007-522179
[Patent Document 8] JP 2001-525342

SUMMARY OF INVENTION

Technical Problem

Against the above background, one of the objective of the present invention is to provide a medium for culturing cells containing uridine and N-acetyl-D-mannosamine at predetermined concentrations for elevating the content of sialic acid in a glycoprotein expressed by using the cells transformed with a gene encoding the glycoprotein.

Technical Solution

In the study directed to the above objective, the present inventors found that a highly silylated erythropoietin is obtained by culturing mammalian cells (CHO cells) transformed with a gene encoding erythropoietin in the medium containing uridine and N-acetyl-D-mannosamine, having completed the present invention.

Thus, the present invention provides what follows.
(1) A medium comprising uridine at a concentration of 0.5 to 10 mM and N-acetyl-D-mannosamine at a concentration of 1 to 15 mM for expressing a glycoprotein by culturing cells.
(2) The medium according to (1) above, wherein the concentration of uridine is 1 to 8 mM and the concentration of N-acetyl-D-mannosamine is 4 to 12 mM.
(3) The medium according to (1) above, wherein the concentration of uridine is 2 to 5 mM and the concentration of N-acetyl-D-mannosamine is 5 to 10 mM.
(4) The medium according to (1) above, wherein the concentration of uridine is about 3 mM and the concentration of N-acetyl-D-mannosamine is about 8 mM.
(5) The medium according to one of (1) to (4) above, further comprising L-alanyl-L-glutamine.
(6) The medium according to (5) above, wherein the concentration of L-alanyl-L-glutamine is 0.5 to 5 mM.
(7) The medium according to (5) above, wherein the concentration of L-alanyl-L-glutamine is 1 to 3 mM.
(8) The medium according to (5) above, wherein the concentration of L-alanyl-L-glutamine is about 2 mM.
(9) The medium according to one of (1) to (8) above, wherein the medium does not comprise serum.
(10) The medium according to one of (1) to (9) above, wherein the cells are selected from the group consisting of mammalian cells, plant cells, and insect cells.
(11) The medium according to (10) above, wherein the cells are the mammalian cells.
(12) The medium according to (11) above, wherein the mammalian cells are CHO cells.
(13) A method for production of the glycoprotein, comprising culturing cells transformed with an exogenous DNA encoding the glycoprotein in the medium according to one of (1) to (10) above.
(14) The method for production according to (13) above, wherein the exogenous DNA encoding the glycoprotein is incorporated into an expression vector to let the glycoprotein express in the transformed cells.
(15) The method for production according to (13) or (14) above, wherein the exogenous DNA encoding the glycoprotein is a human-derived DNA.
(16) The method for production of the glycoprotein comprising culturing the mammalian cells transformed with the exogenous DNA encoding the glycoprotein in the medium according to (11) or (12) above.
(17) The method for production according to (16) above, wherein the exogenous DNA encoding the glycoprotein is incorporated into an expression vector to let the glycoprotein express in the transformed mammalian cells.
(18) The method for production according to (16) or (17) above, wherein the exogenous DNA encoding the glycoprotein is a human-derived DNA.
(19) The method for production according to one of (16) to (18) above, wherein the mammalian cells are incubated at temperature of 36 to 37° C., and then incubated at temperature of 30 to 35° C.
(20) The method for production according to one of (16) to (18) above, wherein the mammalian cells are incubated at temperature of 36 to 37° C., and then incubated at temperature of 31 to 33° C.
(21) The method for production according to one of (16) to (18) above, wherein the mammalian cells are incubated at temperature of 36 to 37° C., and then incubated at temperature of about 32° C.
(22) The method for production according to one of (13) to (21) above, wherein the glycoprotein is selected from the group consisting of; lysosomal enzymes such as α-galactosidase A, acid sphingomyelinase, lysosomal acid lipase, N-acetylgalactosamine-4-sulfatase, hexosaminidase, α-N-acetylgalactosaminidase, α-mannosidase, iduronate-2-sulfatase, glucocerebrosidase, galsulfase, α-L-iduronidase, sialidase, and acid α-glucosidase; tissue plasminogen activator (t-PA); blood coagulation factors such as blood coagulation factor VII, blood coagulation factor VIII, blood coagulation factor IX; lymphokines such as interleukin-6; growth factors such as granulocyte-colony stimulating factor (G-CSF), granulocyte macrophage colony-stimulating factor (GM-CSF), and macrophage colony-stimulating factor (M-CSF); erythropoietin; interferon; thrombomodulin; follicle stimulating hormone; DNaseI; thyroid stimulating hormone (TSH); mouse antibody; humanized mouse antibody; human/mouse chimeric antibody; human antibody; PD-1; PD-1 ligand; and follicle stimulating hormone.
(23) The method for production according to one of (13) to (21) above, wherein the glycoprotein is erythropoietin.
(24) The method for production according to one of (13) to (23) above, wherein the glycoprotein is that contains sialic acid in its glycan.
(25) The method for production according to one of (13) to (24) above, further comprising a step for collecting a culture after the culturing, and subsequently removing the mammalian cells from the collected culture to prepare a culture supernatant containing the glycoprotein.

Effect of Invention

The present invention enables production of a highly sialylated glycoprotein. In general the highly sialylated glycoprotein exhibits prolonged half-life in blood when administered into human blood as a medicament, therefore the glycoprotein produced thereby can be provided as a long-term stable medicament.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
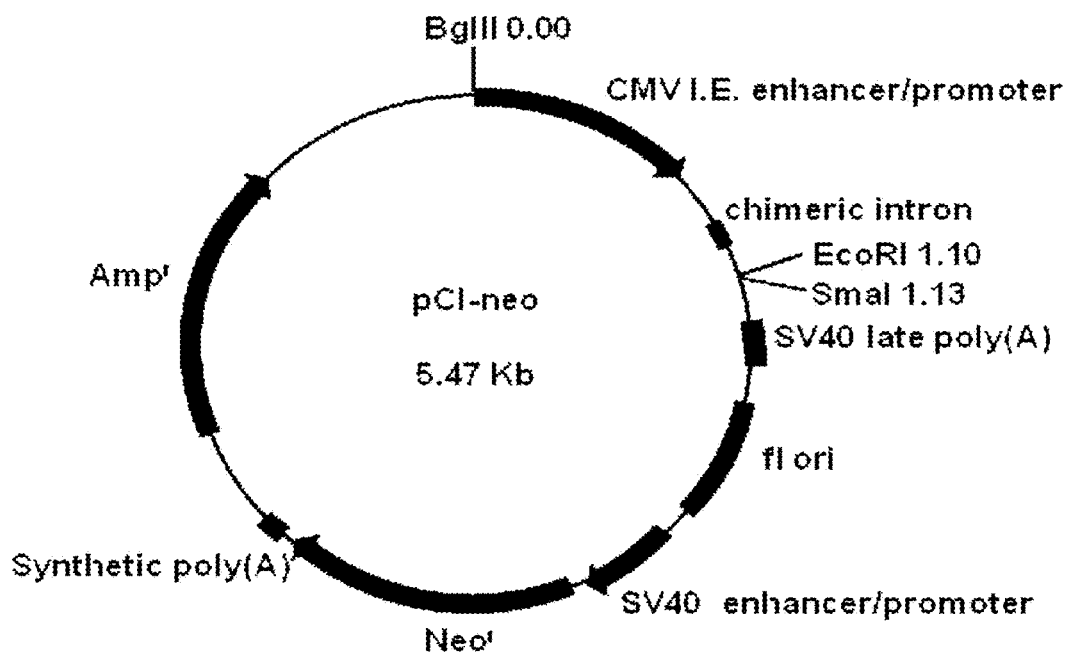
FIG. 1 illustrates pCI-neo vector into which a DNA encoding human erythropoietin is to be incorporated.

The embodiments will now be described with reference to the accompanying drawings, wherein like reference numerals designate corresponding or identical elements throughout the various drawings.

In the present invention, the term "glycoprotein" means the generic name for a group of molecules made up by a covalent linkage between a protein and a sugar. The covalent linkage between the sugar and the protein includes N-glycosidic bond where N-acetyl-D-glucosamine is covalently linked to asparagine residue composing the protein (N-linked glycan), and O-glycosidic bond where N-acetyl-D-galactosamine is covalently linked to serine or threonine residue composing the protein (O-linked glycan), but the mode of linkage between the sugar and the protein in the present invention is not particularly limited. A glycoprotein containing either N-linked glycan of O-linked glycan, and a glycoprotein containing both of them are also categorized as the glycoproteins in the present invention.

Such glycoproteins include; lysosomal enzymes such as α-galactosidase A, acid sphingomyelinase, lysosomal acid lipase, N-acetylgalactosamine-4-sulfatase, hexosaminidase, α-N-acetylgalactosaminidase, α-mannosidase, iduronate-2-sulfatase, glucocerebrosidase, galsulfase, α-L-iduronidase, sialidase, and acid α-glucosidase; tissue plasminogen activator (t-PA); blood coagulation factors such as blood coagulation factor VII, blood coagulation factors VIII, and blood coagulation factor IX; lymphokines such as interleukin-6; growth factors such as granulocyte-colony stimulating factor (G-CSF), granulocyte macrophage colony-stimulating factor (GM-CSF), and macrophage colony-stimulating factor (M-CSF); erythropoietin; interferon; thrombomodulin; follicle stimulating hormone; DNaseI; thyroid stimulating hormone (TSH); mouse antibodies, humanized mouse antibody, human/mouse chimeric antibodies, human antibodies, and such antibodies as including a variety of antibody drugs; PD-1; PD-1 ligand; and follicle stimulating hormone, but are not limited to them.

The glycoprotein of the present invention preferably contains sialic acid in its glycan. The average number of molecules of sialic acid per glycoprotein molecule is preferably one or more.

And in the present invention, when the term "a gene encoding a glycoprotein" or "an exogenous DNA encoding a glycoprotein" is referred, there is no particular limitation as to the origin of the gene or the exogenous DNA, but preferably the origin is mammalians including human, bovine, horse, other domestic animals, dog, cat, and other pet animals. Most practically the origin is human. And the term "a gene encoding a glycoprotein" or "an exogenous DNA encoding a glycoprotein" further includes a gene or an exogenous DNA introduced wherein a mutation for the purpose, for example, to optimize the amount of an expressed glycoprotein encoded by the gene or the exogenous DNA In the present invention, the term "glycoprotein" includes not only a naturally occurring glycoprotein, but also an analogue of the naturally occurring glycoprotein wherein one or more of amino acid residues are substituted for, deleted from, inserted into, or/and added to. The term "glycoprotein" in the present invention further includes, for example, a chimeric protein wherein the domains derived from two or more of naturally occurring glycoproteins or the analogues thereof are combined, and a protein which does not naturally exist, provided that a glycan and a protein are covalently combined therein.

In the present invention, the term "recombinant glycoprotein protein" means the glycoprotein produced by using the cells which are artificially constructed to let the gene or the exogenous DNA encoding the glycoprotein strongly express and to let the expression status maintain. In general, the gene or the exogenous DNA to be strongly expressed may be introduced by transforming the host cells, e.g. mammalian cells, with the expression vector into which the gene or the exogenous DNA is incorporated. But not limited to this, the gene to be strongly expressed may also be an endogenous gene artificially modified to achieve a potent expression. An example for the method of artificially modifying the endogenous gene may be, but are not limited to, the method wherein the endogenous gene in itself is modified. For example, induction of strong expression of the gene may be achieved by substituting the promoter inducing strong gene expression for the endogenous promoter located upstream of the endogenous gene. Such examples have been disclosed in several prior arts (e.g., WO94/12650, and WO95/31560).

In the present invention, as a expression vector for an expression of either a gene or an exogenous DNA encoding the glycoprotein, it is a general practice to employ the expression vector in which a gene encoding a glycoprotein of interest is incorporated downstream of a gene regulatory site that induces a potent expression of a gene, such as a cytomegalovirus (CMV)-derived promoter, SV40 early promoter (SV40 enhancer/promoter), elongation factor 1α (EF-1α) promoter, and human ubiquitin C promoter. Examples of the promoters to be used for the induction of a strong gene expression, that promoters may be substituted for an endogenous promoter to achieve the potent expression of the endogenous gene, include a cytomegalovirus (CMV)-derived promoter, SV40 early promoter (SV40 enhancer/promoter), elongation factor 1α (EF-1α) promoter, and human ubiquitin C promoter.

It is a general practice to use mammalian cells as the cells to be transformed with an expression vector incorporating either a gene or exogenous DNA encoding a glycoprotein or as the cells to be modified for potent expression of the endogenous gene by introducing modification to the endogenous gene. But plant cells, insect cells, yeast or the like may also be used. That is, in the present invention, when referred simply as "cell", the term widely includes a plant cell, an insect cell, a mammalian cell, yeast, and other eukaryotic cells, but it means preferably a plant cell, an insect cell, a mammalian cell, or yeast, more preferably a plant cell, an insect cell, or a mammalian cell, and still more preferably a mammalian cell.

There is no particular limitation as to mammalian cells to be used so long as they can express an intended recombinant glycoprotein. They may be primary culture cells of those collected from organs, muscle tissues, skin tissues, connective tissue, nerve tissue, blood, bone marrow, and the like excised from the body, or their subcultured cells or cell lines established so as to keep their characteristics through repeated subcultures. Those cells may be either normal cells or the cells which have become cancerous. The cells which can be used particularly preferably are CHO cells derived from the ovary of a Chinese hamster; NS/0 cells derived from the mouse myeloma; human fibroblasts; and COS cells derived from the renal fibroblast of an African green monkey. When a recombinant glycoprotein is expressed by using CHO cells, ordinarily a recombinant glycoprotein can be obtained having N-glycoside-linked sugar chain.

In the present invention, the medium used for culturing cells for the expression of a glycoprotein may be the medium supplemented with uridine and N-acetyl-D-mannosamine. However, as needed, the basic medium supplemented with N-acetyl-D-mannosamine but not with uridine may also be used as the medium for culturing cells to express the glycoprotein in the present inventions. Though there is no particular limitation as to which medium is to be employed as the basic medium, as far as it can be used for culturing cells to express a glycoprotein, but a serum free medium may be preferably used.

An example of serum-free media as describe above is a medium comprises; 3 to 700 mg/mL of amino acids, 0.001 to 50 mg/L of vitamins, 0.3 to 10 g/L of monosaccharides, 0.1 to 10000 mg/L of inorganic salts, 0.001 to 0.1 mg/L of trace elements, 0.1 to 50 mg/L of nucleosides, 0.001 to 10 mg/L of fatty acids, 0.01 to 1 mg/L of biotin, 0.1 to 20 µg/L of hydrocortisone, 0.1 to 20 mg/L of insulin, 0.1 to 10 mg/L of vitamin $B_{12}$, 0.01 to 1 mg/L of putrescine, 10 to 500 mg/L of sodium pyruvate, and water-soluble iron compounds. As desired, it may also include thymidine, hypoxanthine, a conventional pH indicator, and antibiotics.

Further, DMEM/F12 medium, a mixed medium consisting of DMEM and F12, may also be used as a basic serum-free medium. Both of these media are well known to those skilled in the art. As a serum-free medium, DMEM (HG)HAM modified (R5) medium may be used, too, which contains sodium hydrogen carbonate, L-glutamine, D-glucose, insulin, sodium selenite, diaminobutane, hydrocortisone, ferric (II) sulfate, asparagine, aspartic acid, serine, and polyvinyl alcohol. Furthermore, a commercially available serum-free medium may also be used as a basic medium, such as CD OptiCHO™ medium, CHO-S-SFM II medium, CD CHO medium (Life Technologies Inc.), EX-CELL™ 302 medium, EX-CELL™ 325-PF medium (SAFC Biosciences Inc.), and the like.

When a medium containing serum (fetal bovine serum) is used as a basic medium, the concentration of serum in the medium is preferably 5 to 20% (v/v), and more preferably 8 to 12% (v/v).

In the present invention, uridine to be added to the basic medium may be the salt thereof. The amount of uridine added to the basic medium should be properly adjusted depending on the types of the cell to be used, the expression vector to be used, and the glycoprotein to be expressed, but uridine is added at a concentration of preferably 0.5 to 10 mM, more preferably 1 to 8 mM, still more preferably 2 to 5 mM, and further more preferably 3 mM in the basic medium. And N-acetyl-D-mannosamine to be added to the basic medium may be the salt thereof. The amount of N-acetyl-D-mannosamine added to the basic medium should be properly adjusted depending on the types of the cell to be used, the expression vector to be used, and the glycoprotein to be expressed, but N-acetyl-D-mannosamine is added at a concentration of preferably 1 to 15 mM, more preferably 4 to 12 mM, still more preferably 5 to 10 mM, further more preferably 5 to 8 mM, and particularly preferably 8 mM in the basic medium.

L-alanyl-L-glutamine or the salt thereof may be added to the basic medium in addition to uridine and N-acetyl-D-mannosamine. The amount of L-alanyl-L-glutamine added to the basic medium should be properly adjusted depending on the types of the cell to be used, the expression vector to be used, and the glycoprotein to be expressed, but L-alanyl-L-glutamine is added at a concentration of preferably 0.5 to 5 mM, more preferably to 3 mM, still more preferably 1.5 to 2.5 mM, and particularly preferably 2 mM in the basic medium.

In the present invention, when a recombinant glycoprotein is produced by culturing mammalian cells transformed with either a gene or an exogenous DNA encoding a glycoprotein, or mammalian cells of which an endogenous promoter is substituted so as to make the endogenous gene strongly express, and by letting the glycoprotein expressed, the culture temperature should be properly adjusted depending on the types of the cells to be used, the expression vector to be used, and the glycoprotein to be expressed. The temperature is adjusted preferably to 30 to 37° C., and more preferably to 36 to 37° C. The culture temperature may be either maintained constant or lowered in a stepwise manner during the culture. When the culture temperature is lowered in a stepwise manner, the culture temperature, for example, may be adjusted to 36 to 37° C. at the start of the culture, and then may be lowered to preferably 30 to 35° C., and more preferably 31 to 33° C., such as 32° C., during the culture period. As most of recombinant glycoproteins are secreted from the cells into the medium, the supernatant containing the recombinant glycoprotein can be obtained by correcting the culture after incubation and removing the mammalian cells from the corrected culture. The recombinant glycoprotein can be purified from the culture supernatant by such a method as chromatography.

EXAMPLES

Though the present invention will be described in further detail below with reference to an example, it is not intended that the present invention be limited to the example.

[Construction of Expression Vector for Human Erythropoietin]

cDNA encoding human erythropoietin was PCR amplified from human fetal liver cDNA library (Clontech Inc.) using the following set of primers:

Primer EPO-5', synthetic sequence (SEQ ID NO:1) and Primer EPO-3', synthetic sequence (SEQ ID NO:2).

In the sequence set forth as SEQ ID NO: 1, nucleotides 3-8 correspond to an EcoRI site, and the nucleotides 9-28 correspond to the first 20 nucleotides of the coding region.

In the sequence set forth as SEQ ID NO: 2, nucleotides 12-17 correspond to a BglII site, and nucleotides 18-30 correspond to the nucleotides 774-762 of the cDNA.

Figure 2:
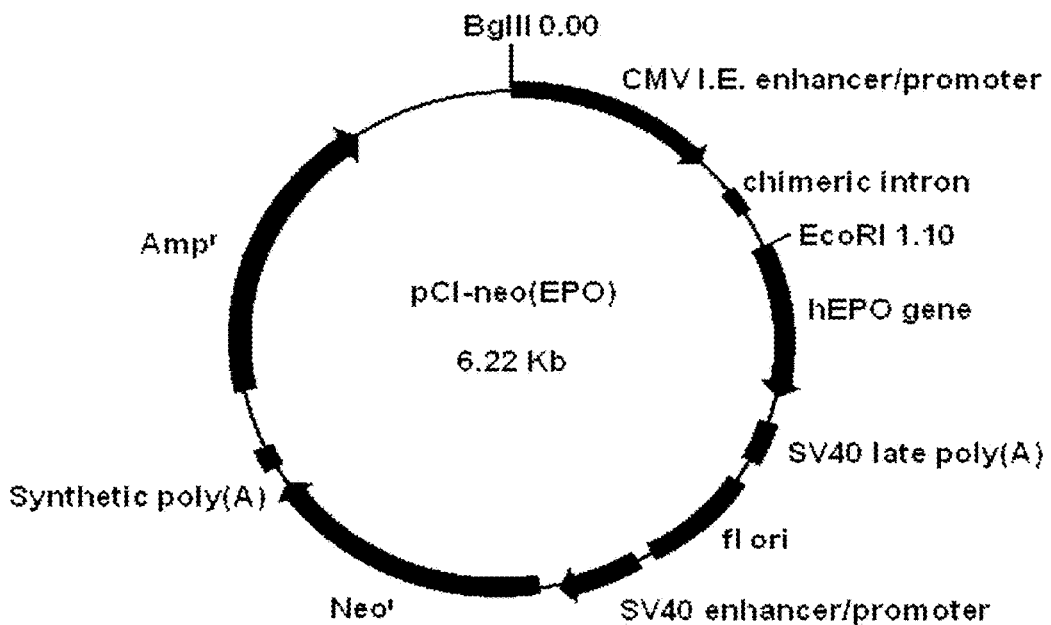
FIG. 2 illustrates pCI-neo (hEPO) vector incorporated a DNA encoding human erythropoietin.

PCR reaction was cycled 30 times with denaturation step at 95° C. for 1 minute, annealing step at 60° C. for 1 minute, and elongation step at 72° C. for 2 minutes. Amplified cDNA was digested with EcoRI and HindIII, and then subcloned between the EcoRI and HindIII sites of the multicloning site of pBluescript vector (pBS: Stratagene Inc.). The resulting vector was digested with BglII, then blunt-ended by T4 DNA polymerase, and subsequently a fragment of human erythropoietin gene was excised by EcoRI digestion. The nucleotide sequence of the obtained fragment of hEPO gene and the encoded amino acid sequence are shown in SEQ ID NO:3 and NO:4, respectively. In SEQ ID NO:3, the nucleotides 9-587 correspond to the region encoding amino acids, nucleotides 3-8 correspond to EcoRI site, and nucleotides 775 to 780 correspond to BglII site. The obtained fragment of hEPO gene was ligated between EcoRI and SmaI sites of pCI-neo vector (Promega Inc., FIG. 1) using DNA ligation kit ver.2 (TAKARA Inc.), and the resulting recombinant vector as shown in FIG. 2 was used as human erythropoietin expression vector pCI-neo (hEPO).

[Establishment of Cells for Expression of Recombinant Human Erythropoietin]

CHO cells (CHO-K1) were purchased from RIKEN, Japan. $1 \times 10^7$ CHO cells were transformed with 20 µg of the above human erythropoietin expression vector using Lipofectamine-2000 (Invitrogen Inc.) in a conventional manner, then the cells were selective-cultured in the Ham-F12 medium (Invitrogen Inc.) supplemented with 10% of fetal bovine serum (FBS) and 0.8 mg/mL of G418 (SIGMA Inc.) to obtain stable transformants which were resistant to neomycin. Then, for habituation of the cells to a serum free medium, the cells were transferred to a commercially available serum-free EX-CELL302 medium (JRH Inc.) supplemented with 4 mM of L-glutamine, 10 mg/L of hypoxanthine, 4 mg/L of thymidine, and 0.12 mg/mL of G418, and continuously cultured until the growth of cells became stable. The resulting cells were suspended in Ham-F12 medium supplemented with 10% of FBS and 10% of DMSO, and stored in liquid nitrogen as master cells.

[Culture of Cells for Expression of Recombinant Human Erythropoietin]

The above master cells stored in liquid nitrogen were quickly thawed in 37° C. thermostatic bath, and suspended in a basic medium, the CD Opti CHO™ medium (Life Technologies Inc.) supplemented with 2 mM of GlutaMAX (Life Technologies Inc.) and 1×HT Supplement (Life Technologies Inc.). Then, the cells were precipitated by centrifugation and corrected. The corrected cells were suspended with the basic medium to obtain the cell suspension, and the number of the living cells was counted. The cell suspension was diluted to the living cell density of $2 \times 10^5$ cells/mL with the basic medium. The cell suspension was dispensed into culture vessels by 120 mL each to generate four groups and incubated for five days at 37° C. under 5% $CO_2$. This incubation was conducted by using Bio Jr.8 (100 mL×8 vessels culture device, AbleBiott Inc.), and pH of the medium was kept at 6.9 and the dissolved oxygen level (DO) was kept at 40% during the incubation. At this time, uridine and N-acetyl-D-mannosamine were added at the concentration as shown in Table 1 to each of the groups (group 1 to group 4). The incubation was conducted four times for each of the groups.

TABLE 1

Concentrations of uridine and N-acetyl-D-mannosamine in the medium of each of the groups (mM)

| group | N-acetyl-D-mannosamine | uridine |
|---|---|---|
| 1 | 0 | 0 |
| 2 | 8 | 0 |
| 3 | 0 | 3 |
| 4 | 8 | 3 |

[Purification of Human Erythropoietin]

On the fifth day of the incubation above, 10 mL of each of the cultures was corrected to centrifuging tubes and centrifuged at 3,000 rpm for 10 minutes. Then, the culture supernatants were corrected and diluted 1.5 times with purified water. Then, 7.5 mL of each of these diluted culture supernatants was loaded on Capto™ adhere column, a multi-modal anion exchange resin (column volume: 1 mL, GE Healthcare Bioscience Inc.) pre-equilibrated with 20 mM Tris buffer (pH 7.5). After washing the column with 5 column volumes of 20 mM Tris buffer (pH 7.5), recombinant human erythropoietin adsorbed by the resin was eluted with 20 mM Tris buffer (pH 7.5) containing 200 mM of NaCl to obtain eluted fractions. And the eluted fractions were concentrated by Amicon Ultra-4 Centrifugal Filter Units (molecular weight cut off: 3 kDa, Millipore Inc.) to 100 µL of volume.

[Analysis of Recombinant Human Erythropoietin]

The concentrated solution of each of the groups was subjected capillary electrophoresis by using Bare Fused-Silica Capillary (50 µm ID, 375 µm OD, 50 cm length, Beckmann Coulter Inc.) attached to capillary electrophoresis system (P/ACE™ system MDQ, Beckmann Coulter Inc.). In doing this, 10 mM Tris buffer (pH 4.5) containing 10 mM of sodium chloride, 500 mM of sodium acetate, 7 M of urea, and 2.5 mM of putrescine was used as an electrophoresis buffer, and the electrophoresis was performed at constant current of 24 µA for 50 minutes. Further the wave length at 214 nm was monitored by an UV detector to detect the recombinant human erythropoietin subjected to the electrophoresis.

[Results of Analysis of Recombinant Human Erythropoietin]

The isoform showing the lowest isoelectric point among the isoforms showing different isoelectric points when detected by the capillary electrophoresis above was named as type I, and further the isoforms were named as type II and type III in ascending order of isoelectric point. The ratios of type I, type II, and type III to sum of all of detected isoforms were calculated, respectively. And the ratios were compared between the groups. The ratios of type I, type II, and type III in each group were shown in FIG. 3. The ratios of type I, type II, and type III in the recombinant human erythropoietin of the group 1 obtained by culturing the cells in the basic medium were about 0.7%, about 5%, and about 15%, respectively (FIG. 3).

Figure 3:
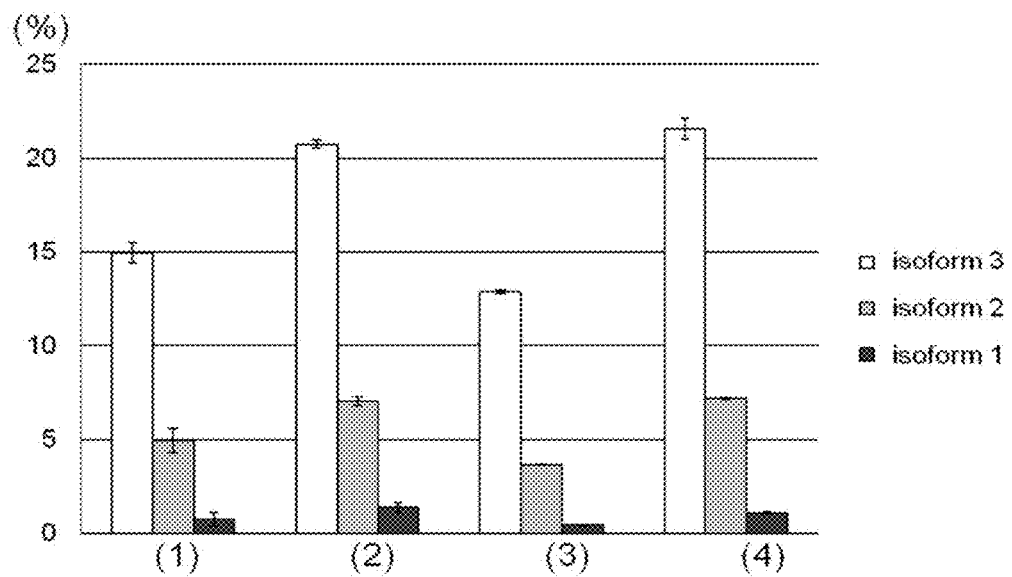
FIG. 3 shows the ratios of each of isoforms (type 1 to type 3) in the recombinant human erythropoietin obtained by culturing cells for expression of recombinant human erythropoietin in a variety of mediums. The vertical axis shows the ratios of isoforms (%). Error bars indicate standard deviations (n=4). Graph (1) shows that obtained by culturing in the basic medium, Graph (2) shows that obtained by culturing in the basic medium added with 8 mM of N-acetyl-D-mannosamine, Graph (3) shows that obtained by culturing in the basic medium added with 3 mM of uridine, Graph (4) shows that obtained by culturing in the basic medium added with 8 mM of N-acetyl-D-mannosamine and 3 mM of uridine, respectively.

In contrast, in the group 2 obtained by culturing the cells in the basic medium added with only 8 mM of N-acetyl-D-mannosamine, the ratios of type I, type II, and type III were about 1.2%, about 7%, and about 20.7%, respectively (FIG. 3). The isoelectric point of isoforms of the recombinant human erythropoietin is lowered in accordance with the increase of the number of sialic acid molecules added per molecule of recombinant human erythropoietin. Therefore, the above results shows that the number of sialic acid molecules added per molecule of recombinant human erythropoietin of the group 2 obtained by adding 8 mM of N-acetyl-D-mannosamine to the basic medium is more than that obtained by using the basic medium.

In contrast of this, in the group 3 obtained by culturing the cells in the basic medium added with only 3 mM of uridine, the ratios of type I, type II, and type III markedly decreased when compared with those of the group 3 obtained by culturing the cells in the basic medium, and were about 0.3%, about 3.5%, and about 13%, respectively (FIG. 3). These results show that the number of molecules of sialic acid added per molecule of recombinant human erythropoietin of the group 3 obtained by adding 3 mM of uridine to the basic medium decreases when compared with that obtained by using the basic medium.

Figure 4:
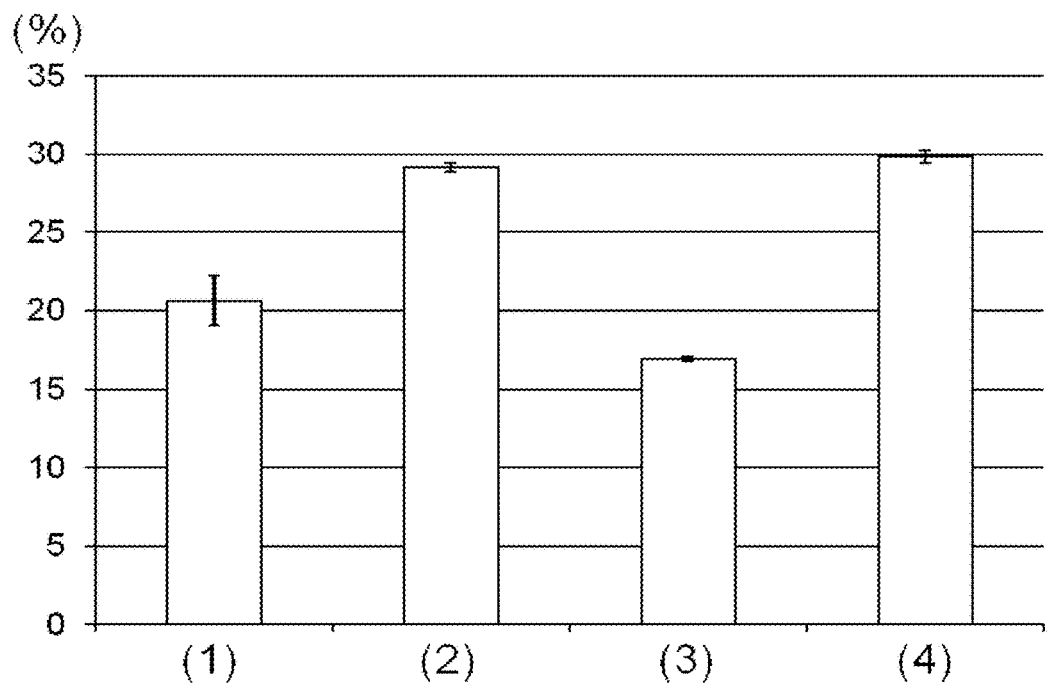
FIG. 4 shows the sum of the ratio of isoforms type 1 to type 3 in the recombinant human erythropoietin obtained by culturing cells for the expression of recombinant human erythropoietin in a variety of mediums. The vertical axis shows the ratios (%). Graph (1) shows that obtained by culturing in the basic medium, Graph (2) shows that obtained by culturing in the basic medium added with 8 mM of N-acetyl-D-mannosamine, Graph (3) shows that obtained by culturing in the basic medium added with 3 mM of uridine, Graph (4) shows that obtained by culturing in the basic medium added with 8 mM of N-acetyl-D-mannosamine and 3 mM of uridine, respectively.

Furthermore, in the group 4 obtained by culturing the cells in the basic medium added with 8 mM N-acetyl-D-mannosamine and 3 mM of uridine, the ratios of type I, type II, and type III were about 1.1%, about 7%, and about 21.5%, respectively (FIG. 3). When comparing the sum of the ratios of type I, type II, and type III between the group 4 and the group 2, the group 4 exceeds the group 2, which indicates that the number of molecules of sialic acid added per molecule of recombinant human erythropoietin can be further increased by adding 8 mM of N-acetyl-D-mannosamine concomitantly with 3 mM of uridine (FIG. 4). Such a synergistic effect of N-acetyl-D-mannosamine and uridine is surprising when considering that the number of molecules of sialic acid added per molecule of recombinant human erythropoietin of the group 3 obtained by adding only 3 mM of uridine to the medium is less than that obtained by using the basic medium.

[Other Discussions]

From the results of the analysis shown above, it has been elucidated that the number of molecules of sialic acid added per molecule of recombinant human erythropoietin can be increased by culturing the cells transformed with the gene of recombinant human erythropoietin in the medium added with 8 mM of N-acetyl-D-mannosamine or with 8 mM of N-acetyl-D-mannosamine and 3 mM of uridine. It is considered that the number of molecules of sialic acid added per molecule of recombinant human erythropoietin may be increased by the combination of the method of culturing the cells in these medium and another method, for example, a method of culturing cells with the temperature lowered in a stepwise manner during cell culture period.

Figure 5:
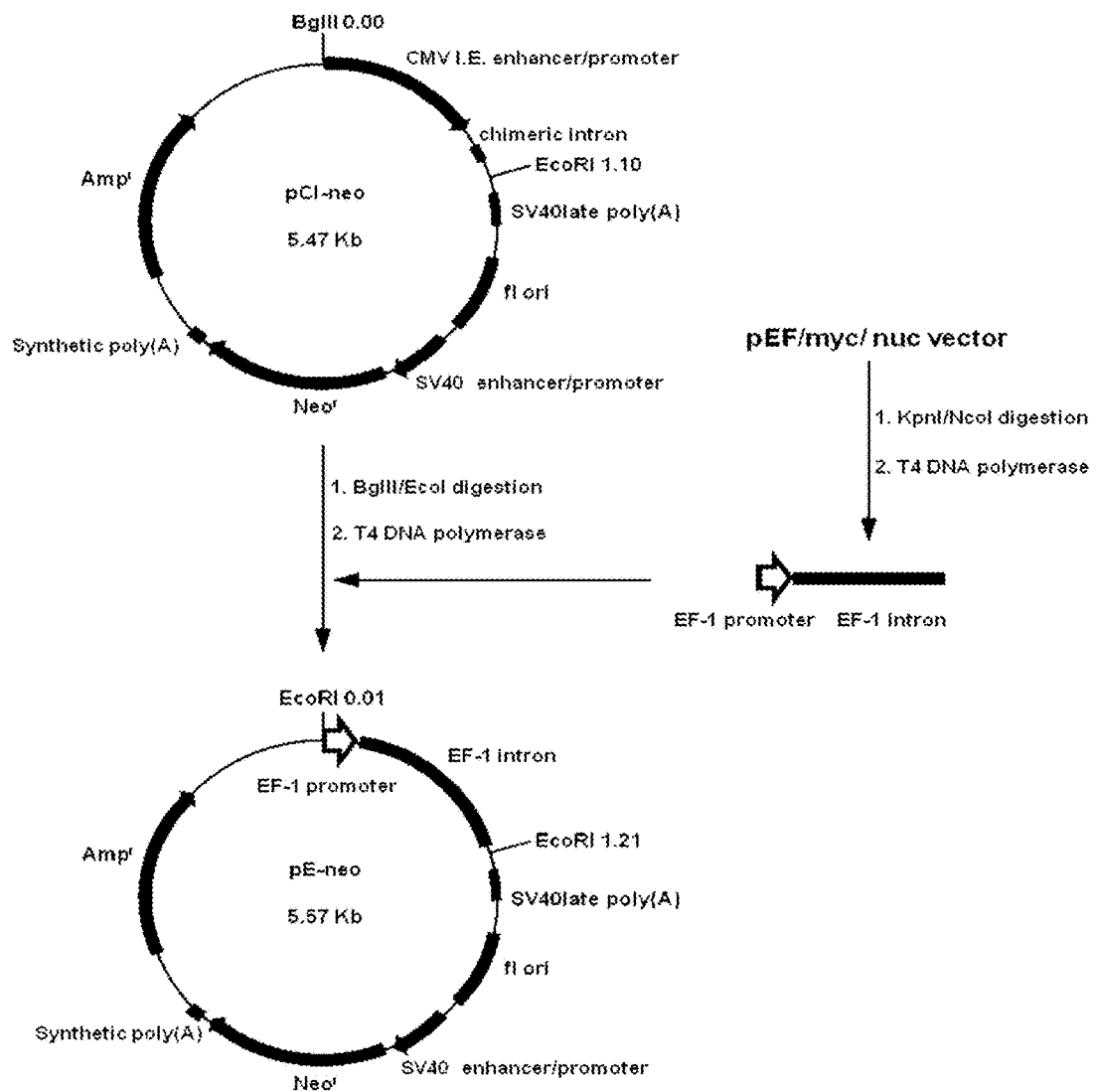
FIG. 5 shows the flow diagram of the method for constructing pE-neo vector.

[Construction of Expression Vector for Human FSH]

pEF/myc/nuc Vector (Invitrogen Inc.) was digested with KpnI and NcoI to cut out a region including the EF-1α promoter and its first intron, which then was blunt-ended with T4 DNA polymerase. Vector pCI-neo (Invitrogen Inc.) was digested with BglII and EcoRI to cut out a region including the CMV enhancer/promoter and the intron, which then was blunt-ended with T4 DNA polymerase. Into this was inserted the above-mentioned region including the EF-1α promoter and its first intron to give pE-neo vector (FIG. 5).

Figure 6:
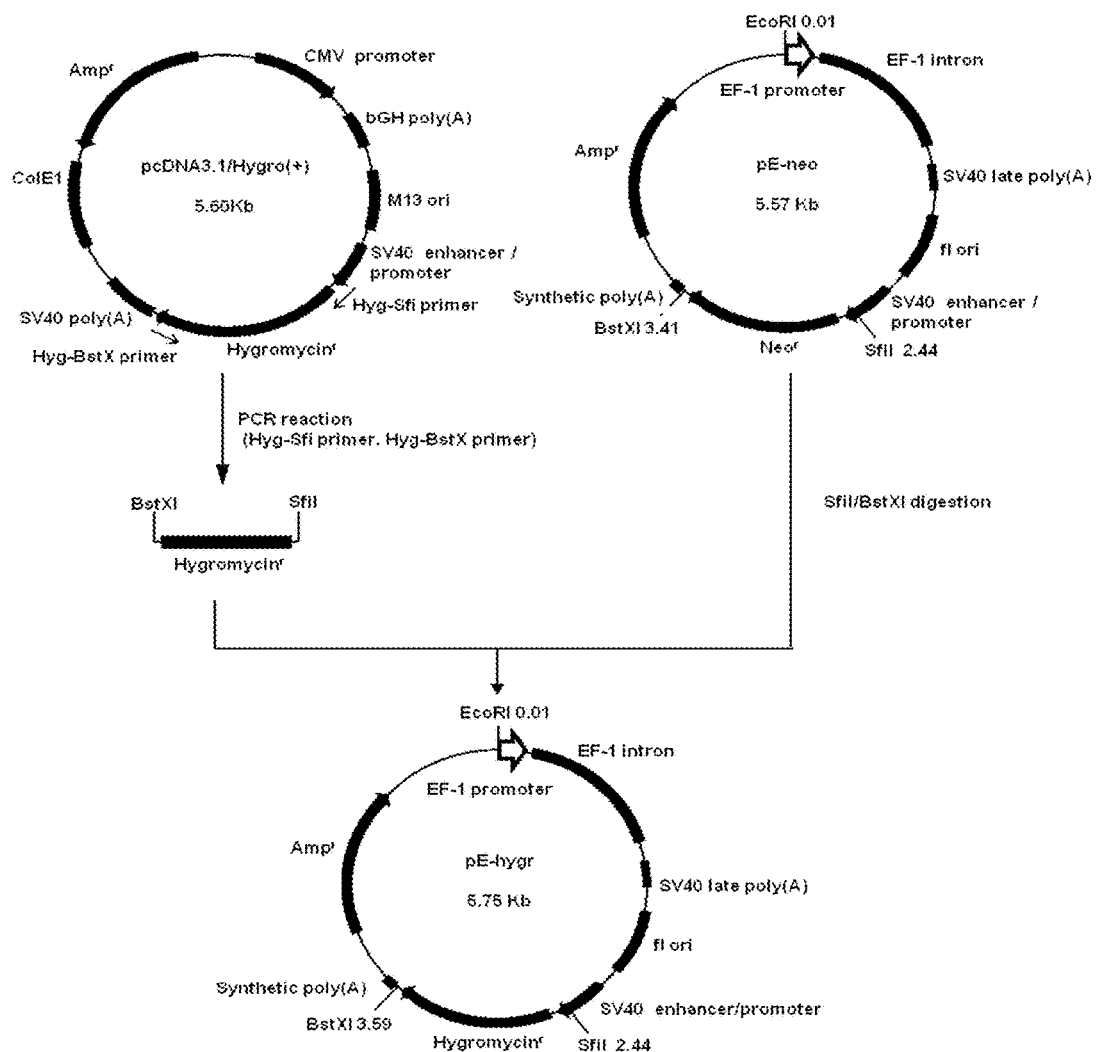
FIG. 6 shows the flow diagram of the method for constructing pE-hygr vector.

The vector pE-neo was digested with SfiI and BstXI to remove a region of about 1 kbp including the neomycin resistance gene (FIG. 6). Using pcDNA3.1/Hygro (+) (Invitrogen Inc.) as a template, the hygromycin gene was amplified by PCR with primer Hyg-Sfi (SEQ ID NO: 5) and primer Hyg-BstX (SEQ ID NO:6) (FIG. 6). The hygromycin gene thus amplified was digested with SfiI and BstXI, and then inserted into the aforementioned pE-neo vector to form pE-hygr vector (FIG. 6).

Using a human placenta cDNA library (Takara Bio Inc.) as a template, a primary PCR was performed with primer HCG-A-F (SEQ ID NO:7) and primer HCG-A-R (SEQ ID NO:8). Then, using the PCR product thus obtained, a secondary PCR was performed to amplify the human FSHα chain cDNA, with primer HCGA-ORF-F (SEQ ID NO:9), which had a sequence located a little downstream of 3'-end of primer HCG-A-F used in the primary PCR, and with primer HCGA-ORF-R (SEQ ID NO:10), which had a sequence located a little upstream of 5'-end of primer HCG-A-R used in the primary PCR. In the same manner, using a human pituitary gland cDNA library (Takara Bio Inc.) as a template, PCR was performed to amplify the human FSHβ chain cDNA, with primary primers FSH-F (SEQ ID NO:11) and FSH-R (SEQ ID NO:12) and then secondary primers FSH-F2 (SEQ ID NO:13) and FSH-R2 (SEQ ID NO: 14).

The primary PCR for human FSHα chain was performed using 100 ng of the human placenta cDNA library as a template and running 40 cycles of reactions each of which consisted of "95° C./10 sec, 55° C./10 sec, and 72° C./10 sec". The secondary PCT was performed using 1 µL of the reaction mixture of the primary PCR as a template and running 30 cycles of reactions each of which consisted of "95° C./10 sec, 60° C./10 sec, and 72° C./10 sec". And the primary PCR for human FSHβ chain was performed using 10 ng of a human pituitary gland cDNA library as a template and running 40 cycles of reactions each of which consisted of "98° C./2 sec, 60° C./10 sec, and 72° C./10 sec" The secondary PCR was performed using 1 µL of the reaction mixture of the primary PCR as a template and running 30 cycles of reactions each of which consisted of "98° C./2 sec, 60° C./10 sec, and 72° C./10 sec".

Figure 7:
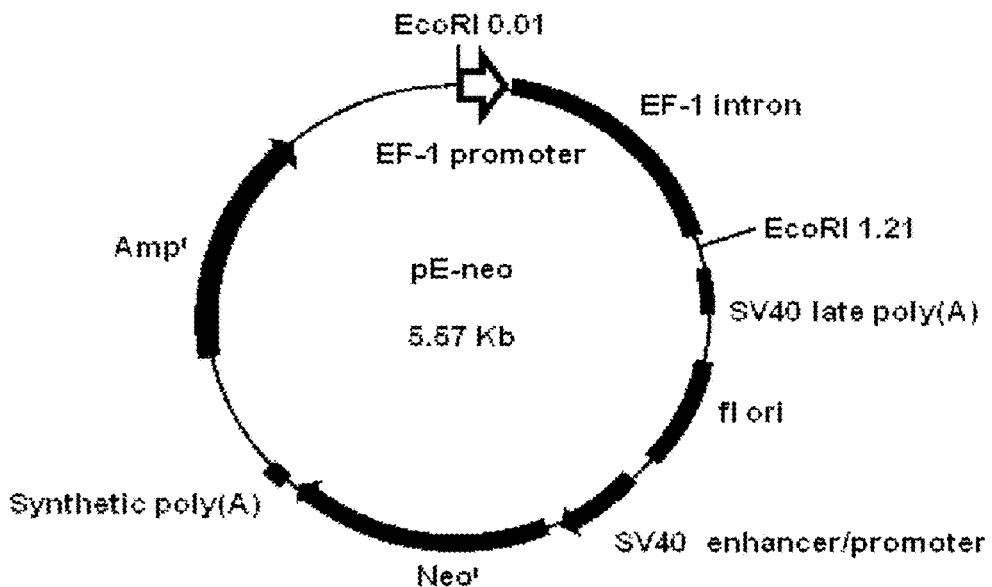
FIG. 7 illustrates pE-Neo (FSHα) vector incorporated a DNA encoding a chain of human FSH α-chain.

The human FSHα chain cDNA thus amplified was digested with EcoRI and inserted into the EcoRI site of pBluescriptIISK (−) (pBS: Stratagene Inc.) which had been digested with EcoRI. The plasmid DNA thus obtained was digested with XbaI and EcoRV to cut out human FSHα-chain cDNA, which then was inserted into the pE-neo vector that had been digested with XbaI and SmaI to form human FSHα-chain expression vector pE-neo (hCGα) (FIG. 7).

Figure 8:
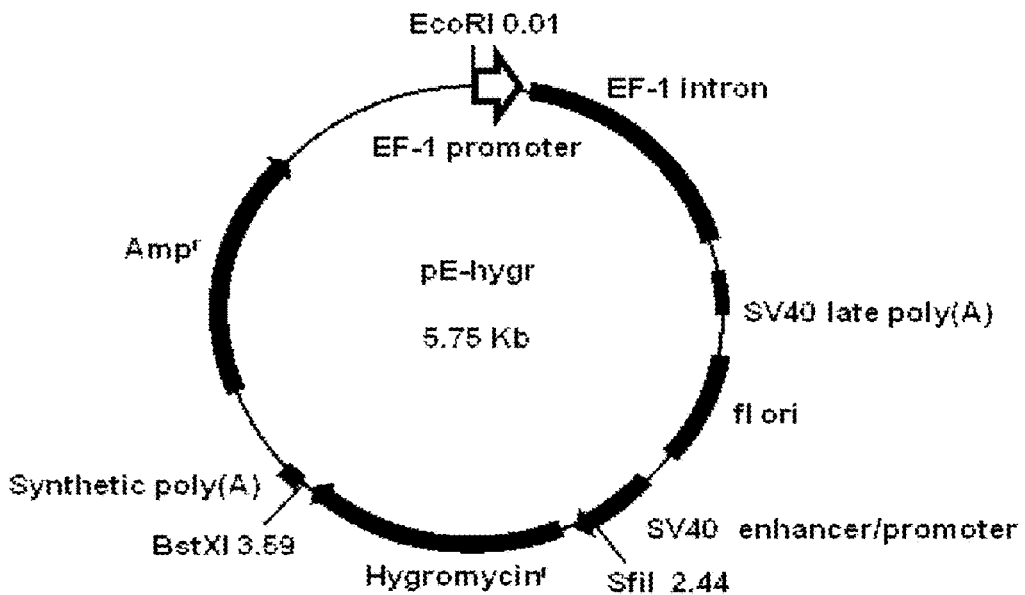
FIG. 8 illustrates pE-hygr (FSHβ) vector incorporated a DNA encoding β chain of human FSH β-chain.

The human FSHβ-chain cDNA amplified above was digested with EcoRI and NotI, and then introduced into pBluescriptIISK (−) which had been digested with EcoRI and NotI. The plasmid DNA thus obtained was digested with EcoRI and, after blunt-ended with T4 DNA polymerase, further digested with NotI to cut out human FSHβ-chain cDNA. The pE-hygr vector was digested with XbaI and, after blunt-ended with T4 DNA polymerase, further digested with NotI. To this pE-hygr vector was introduced human FSHβ-chain cDNA to form human FSH expression vector pE-hygr (FSHβ) (FIG. 8).

[Production of Cells for Expression of Recombinant Human FSH]

CHO cells (CHO-K1: purchased from American Type Culture Collection) was transfected with the above-mentioned expression vector pE-neo (hCGα) and pE-hygr (FSHβ) using Lipofectamine-2000 (Invitrogen Inc.) according to the following method. On the day before transfection, CHO-K1 cells were seeded in a 3.5-cm culture dish so that a cell density might be close to that of a confluent state, and the cells were cultured overnight at 37° C. under a flow of air containing 5% carbon dioxide gas. On the following day, the cells were washed twice with PBS (−), and the medium was replaced with 1 mL of serum-free D-MEM/F12 medium (Invitrogen Inc.). 200 μL of a 1:1 mixture solution consisting of Lipofectamine-2000 solution diluted 20 times with Opti-MEM I medium (Invitrogen Inc.) and a plasmid DNA solution containing 13.2 μg/mL of pE-neo (hCGα) and 6.6 μg/mL of pE-hygr (FSHβ) was added, and transfection was performed at 37° C. for five hours.

After transfection above, the medium was replaced with D-MEM/F12 medium containing 5% FCS (D-MEM/F12/5% FCS), and culture was carried out for 2 days at 37° C. under a flow of air containing 5% carbon dioxide. The medium then was replaced with the D-MEM/F12/5% FCS medium containing 0.6 mg/mL of G418 and 0.4 mg/mL of hygromycin B, and selective culture was carried out at 37° C. under a flow of air containing 5% carbon dioxide. Cells that had grown in the medium for selective culture were subjected to several successive rounds of subculture in the medium to give recombinant cells.

Then, according to the limiting dilution technique, the recombinant cells were seeded on a 96-well plate in such a manner that not more than one cell might be seeded per well, and the cells were cultured for about days to let each of them form a clonal colony. The culture supernatant in each of the wells where a clonal colony was formed was sampled and examined by ELISA for the amount of expressed human FSH, and cell lines which were found expressing a high amount of human FSH were selected.

For habituation to serum-free suspended cell culture, the selected cell lines were successively cultured in a commercially available serum-free medium, EX-CELL302 medium (JRH Inc.) supplemented with 4 mM of L-glutamine, 10 mg/L of hypoxanthine, 4 mg/L of thymidine, 120 mg/L of G148, and 80 mg/L of hygromycin B, until the growth rate of the cells stabilized. Then, the medium was replaced with IS CHO-V-GS medium and the culture was successively carried out until the growth rate of the cells stabilized, and the cells were suspended in IS CHO-V-GS medium supplemented with 10% DMSO, and stored as seed cells in liquid nitrogen.

[Culture of Cells for Expression of Recombinant Human FSH]

The above master cells stored in liquid nitrogen were quickly thawed in 37° C. thermostatic bath, and suspended in a basic medium, the CD Opti CHO™ medium (Life Technologies Inc.) supplemented with 2 mM of GlutaMAX (Life Technologies Inc.) and 1×HT Supplement (Life Technologies Inc.). Then, the cells were precipitated by centrifugation and corrected. The corrected cells were suspended with the basic medium to obtain cell suspension, and the number of the living cells was counted. The cell suspension was diluted to the living cell density of $2 \times 10^5$ cells/mL with the basic medium.

The cell suspension was dispensed into culture vessels by 120 mL each to generate four groups and incubated for five days at 37° C. under 5% $CO_2$. This incubation was conducted by using Bio Jr.8 (100 mL×8 vessels culture device, AbleBiott Inc.), and pH of the medium was kept at 6.9 and the dissolved oxygen level (DO) was kept at 40% during the incubation. At this time, uridine and N-acetyl-D-mannosamine were added at the concentration shown in Table 1 to each of the groups (group 1 to group 4). The incubation was conducted twice for each of the groups.

TABLE 2

Concentrations of uridine and N-acetyl-D-mannosamine in the medium of each of the groups (mM)

| group | N-acetyl-D-mannosamine | uridine |
| --- | --- | --- |
| 1 | 0 | 0 |
| 2 | 8 | 0 |
| 3 | 0 | 3 |
| 4 | 8 | 3 |

[Purification of Recombinant Human FSH]

On the fifth day of the incubation above, 10 mL of each of the cultures was corrected to centrifuging tubes and centrifuged at 3,000 rpm for 10 minutes to correct the culture supernatants. Then, 20 mL of each of the culture supernatants was loaded on CaptureSelect™ FSH, a FSH affinity resin (column volume: 1 mL, Life Technologies Inc.) pre-equilibrated with PBS (pH 7.4). After washing the column with five column volumes of PBS (pH 7.4), recombinant human FSH adsorbed by the resin was eluted with 20 mM Tris buffer (pH 7.4) containing 2M of $MgCl_2$ to obtain eluted fractions. The eluted fractions were diluted with water and repeatedly concentrated by using Amicon Ultra-4 Centrifugal Filter Units (molecular weight cut off: 3 kDa, Millipore Inc.). Finally the eluted fractions were concentrated to 100 μL of volume to obtain the concentrated solutions of the purified recombinant human FSH for each of the groups (the group 1 to the group 4). The concentration of recombinant human FSH in the purified recombinant human FSH was adjusted to 1 mg/mL.

[Measurement of Sialic Acid Content]

50 μL of the concentrated solution of the purified recombinant human FSH of each of the groups was alkali-treated with 0.3M sodium hydroxide at 37° C. for 30 minutes, subsequently was acid-treated with 0.05M hydrochloric acid at 80° C. for 60 minutes to make glycans composing recombinant human FSH hydrolyzed to monosaccharides. Then, the solution were added with fluorescence reagent (a solution containing 9.6 mM of 1,2-diamino-4,5-methylenedioxybenzene dihydrochloride, 24 mM of sodium hydrosulfite, and 1M of 2-mercaptoethanol), and heated at 50° C. for 150 minutes to fluorescently label the monosaccharides obtained by the hydrolysis. The reaction solutions thus obtained were used as sample solutions. As a standard, sialic acid was concurrently treated with the same manner, and the standard of fluorescence-labeled sialic acid was obtained. The standard thus obtained was analyzed by HPLC using COSMOSIL $5C_{18}$-PAQ as reverse phase column, and the elution time of sialic acid, the time when the peak corresponding to sialic acid appeared, was measured. And each of the sample solutions was analyzed by HPLC and the area of peak corresponding to sialic acid was calculated.

Figure 9:
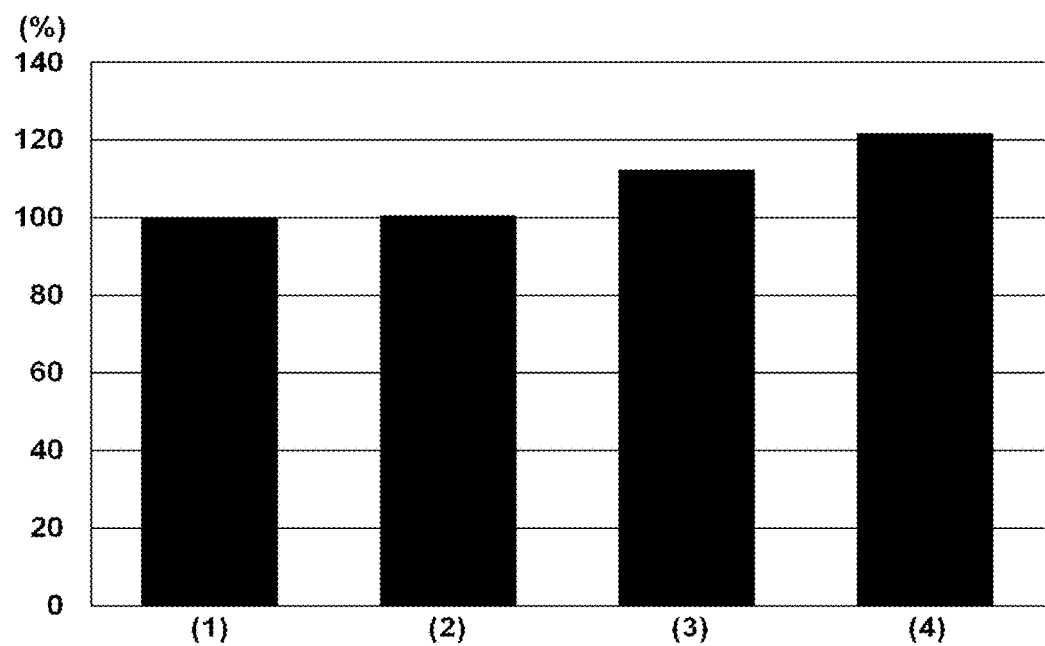
FIG. 9 shows the relative value (%) of sialic acid content in recombinant human FSH obtained by culturing cells for the expression of recombinant human FSH in a variety of mediums, when the sialic acid content in recombinant human FSH obtained by culturing in the basic medium is referred to as 100%. Graph (1) shows that obtained by culturing in the basic medium, Graph (2) shows that obtained by culturing in the basic medium added with 8 mM of N-acetyl-D-mannosamine, Graph (3) shows that obtained by culturing in the basic medium added with 3 mM of uridine, Graph (4) shows that obtained by culturing in the basic medium added with 8 mM of N-acetyl-D-mannosamine and 3 mM of uridine, respectively.

Relative values (%) of peak areas of the group 2 and the group 3 were calculated relative to the peak area of the group 1, obtained by culturing the cells in the basic medium, whose peak area was regarded as 100% (FIG. 9). As the result, the peak area of the group 2, wherein the cells were cultured in the basic medium added with 8 mM of N-acetyl-D-mannosamine, was nearly about 100%. In contrast, peak area of the group 3, wherein the cells were cultured in the medium added with 3 mM of uridine was about 112%, showing that the average number of sialic acid molecules per molecule of recombinant human FSH increased by about 10% when the cells were cultured in the medium added with 3 mM of uridine. Further, the peak area of the group 4, wherein the cells were cultured in the medium added with 8 mM N-acetyl-D-mannosamine and 3 mM uridine to the basic medium, was about 121%, showing that the average number of sialic acid molecules per molecule of recombinant human FSH obtained by culturing the cells in the medium added with 8 mM of N-acetyl-D-mannosamine and 3 mM of uridine was increased by about 20%, when comparing with that of recombinant human FSH obtained by culturing the cells in the basic medium.

In the case of recombinant human erythropoietin, the number of molecules of sialic acid added per molecule of recombinant human erythropoietin of the group 3, wherein only 3 mM of uridine was added to the medium, decreased when compared with that obtained by culturing in the basic medium. In contrast, in the case of recombinant human FSH, the number of molecules of sialic acid added per molecule of recombinant human FSH of the group 3, wherein only 3 mM of uridine was added to the medium, increased when compared with that obtained by culturing in the basic medium. On the other hand, the number of molecules of sialic acid added per molecule of recombinant human FSH of the group 2, wherein only 8 mM of N-acetyl-D-mannosamine was added to the medium, was almost equal to that obtained by culturing in the basic medium.

However, both of recombinant human erythropoietin and recombinant human FSH, obtained by culturing the cells in the medium containing 8 mM of N-acetyl-D-mannosamine and 3 mM of uridine, showed higher sialic acid content than those obtained by using the basic medium, indicating that by culturing the cells in the medium supplemented with these two elements for the production of a recombinant glycoprotein, the number of molecules of sialic acid added per the molecule can be increased regardless of the types of glycoproteins.

OTHER DISCUSSIONS

From the results of the analysis shown above, it has been elucidated that the number of sialic acid molecules added per molecule of recombinant glycoprotein can be increased by culturing the cells transformed with a gene or an exogenous DNA encoding a glycoprotein of interest in a medium added with 8 mM of N-acetyl-D-mannosamine and 3 mM of uridine. It is considered that the number of molecules of sialic acid added per molecule of recombinant glycoprotein may be increased by the combination of the method of culturing the cells in such a medium and another method, for example, a method of culturing the cells with the temperature lowered in a stepwise manner during the culture period.

INDUSTRIAL APPLICABILITY

According to the present invention, there is provided a long-term stable pharmaceutical comprising a glycoprotein as an active ingredient and showing a prolonged half-life in blood when administered to a body.

Obviously, numerous modifications and variations of the present invention are possible in light of the above teachings. It is therefore to be understood that within the scope of the appended claims, the invention may be practiced otherwise than as specifically described herein.

SEQUENCE LISTING FREE TEXT

SEQ ID NO:1=Primer EPO-5', synthetic sequence
SEQ ID NO:2=Primer EPO-3', synthetic sequence
SEQ ID NO:3=PCR product amplified by Primer EPO-5' and Primer EPO-3'
SEQ ID NO:5=Primer Hyg-Sfi, synthetic sequence
SEQ ID NO:6=Primer Hyg-BstX, synthetic sequence
SEQ ID NO:7=Primer HCG-A-F, synthetic sequence
SEQ ID NO:8=Primer HCG-A-R, synthetic sequence
SEQ ID NO:9=Primer HCGA-ORF-F, synthetic sequence
SEQ ID NO:10=Primer HCGA-ORF-R, synthetic sequence
SEQ ID NO:11=Primer FSH-F, synthetic sequence
SEQ ID NO:12=Primer FSH-R, synthetic sequence
SEQ ID NO:13=Primer FSH-F2, synthetic sequence
SEQ ID NO:14=Primer FSH-R2, synthetic sequence

SEQUENCE LISTING

1195P_ST25

What is claimed is:

1. A cell culture medium comprising:
uridine at a concentration of 0.5 to 10 mM; and
N-acetyl-D-mannosamine at a concentration of 1 to 15 mM, wherein, when a recombinant glycoprotein is produced in said cell culture medium, the average number of sialic acid molecules per molecule of said recombinant glycoprotein is about 20% or greater than 20% compared to that produced in a cell culture medium lacking said uridine and said N-acetyl-D-mannosamine.

2. The medium according to claim 1, wherein the concentration of uridine is 1 to 8 mM, and the concentration of N-acetyl-D-mannosamine is 4 to 12 mM.

3. The medium according to claim 1, wherein the concentration of uridine is 2 to 5 mM and the concentration of N-acetyl-D-mannosamine is 5 to 10 mM.

4. The medium according to claim 1, wherein the concentration of uridine is about 3 mM and the concentration of N-acetyl-D-mannosamine is about 8 mM.

5. The medium according to claim 1, further comprising: L-alanyl-L-glutamine.

6. The medium according to claim 5, wherein the concentration of L-alanyl-L-glutamine is 0.5 to 5 mM.

7. The medium according to claim 5, wherein the concentration of L-alanyl-L-glutamine is 1 to 3 mM.

8. The medium according to claim 5, wherein the concentration of L-alanyl-L-glutamine is about 2 mM.

9. The medium according to claim 1, wherein the medium does not include serum.

10. A method of producing a glycoprotein, comprising:
culturing a cell transformed with an exogenous DNA encoding the glycoprotein in the medium according to claim 1.

11. The method according to claim 10, wherein the exogenous DNA encoding the glycoprotein is incorporated into an expression vector such that the glycoprotein is expressed in a transformed cell.

12. The method according to claim 10, wherein the exogenous DNA encoding the glycoprotein is a human-derived DNA.

13. The method according to claim 10, wherein the cell is a mammalian cell.

14. The method according to claim 13, wherein the mammalian cell is a CHO cell.

15. The method according to claim 10, wherein the cell is selected from the group consisting of a mammalian cell, a plant cell, and an insect cell.

16. The method according to claim 13, wherein the exogenous DNA encoding the glycoprotein is incorporated into an expression vector such that the glycoprotein is expressed in a transformed cell.

17. The method according to claim 13, wherein the exogenous DNA encoding the glycoprotein is a human-derived DNA.

18. The method according to claim 13, further comprising:
- incubating the mammalian cell at a temperature of 36 to 37° C.; and subsequently
- incubating the mammalian cell at a temperature of 30 to 35° C.

19. The method according to claim 13, further comprising:
- incubating the mammalian cell at a temperature of 36 to 37° C.; and subsequently
- incubating the mammalian cell at a temperature of 31 to 33° C.

20. The method according to claim 13, further comprising:
- incubating the mammalian cell at a temperature of 36 to 37° C.; and subsequently
- incubating the mammalian cell at a temperature of about 32° C.

21. The method according to claim 10, wherein the glycoprotein is selected from the group consisting of a lysosomal enzyme, a blood coagulation factor, a lymphokine, erythropoietin, interferon, thrombomodulin, DNaseI, thyroid stimulating hormone, mouse antibody, humanized mouse antibody, human/mouse chimeric antibody, human antibody, PD-1, PD-1 ligand, and follicle stimulating hormone.

22. The method according to claim 10, wherein the glycoprotein is selected from the group consisting of α-galactosidase A, acid sphingomyelinase, lysosomal acid lipase, N-acetylgalactosamine-4-sulfatase, hexosaminidase, α-N-acetylgalactosaminidase, α-mannosidase, iduronate-2-sulfatase, glucocerebrosidase, galsulfase, α-L-iduronidase, sialidase, acid α-glucosidase, blood coagulation factor VII, blood coagulation factor VIII, blood coagulation factor IX, interleukin-6, granulocyte-colony stimulating factor, granulocyte macrophage colony-stimulating factor, and macrophage colony-stimulating factor.

23. The method according to claim 10, wherein the glycoprotein is erythropoietin.

24. The method for production according to claim 10, wherein the glycoprotein includes sialic acid in a glycan thereof.

25. The method for production according to claim 10, further comprising:
- collecting a culture after the culturing; and
- removing the mammalian cells from collected culture such that a culture supernatant including the glycoprotein is prepared.

* * * * *

SEQUENCE LISTING

```
<160> NUMBER OF SEQ ID NOS: 14

<210> SEQ ID NO 1
<211> LENGTH: 28
<212> TYPE: DNA
<213> ORGANISM: Artificial Sequence
<220> FEATURE:
<223> OTHER INFORMATION: Primer EPO-5', synthetic sequence

<400> SEQUENCE: 1
ccgaattcat gggggtgcac gaatgtcc                                              28

<210> SEQ ID NO 2
<211> LENGTH: 30
<212> TYPE: DNA
<213> ORGANISM: Artificial Sequence
<220> FEATURE:
<223> OTHER INFORMATION: Primer EPO-3', synthetic sequence

<400> SEQUENCE: 2
tcaagcttct tagatctcag agttgctctc                                            30

<210> SEQ ID NO 3
```

```
<211> LENGTH: 791
<212> TYPE: DNA
<213> ORGANISM: Artificial Sequence
<220> FEATURE:
<223> OTHER INFORMATION: PCR product amplified by Primer EPO-5' and
      Primer EPO-3'

<400> SEQUENCE: 3
ccgaattcat gggggtgcac gaatgtcctg cctggctgtg gcttctcctg tccctgctgt       60
cgctccctct gggcctccca gtcctgggcg ccccaccacg cctcatctgt gacagccgag      120
tcctggagag gtacctcttg gaggccaagg aggccgagaa tatcacgacg ggctgtgctg      180
aacactgcag cttgaatgag aatatcactg tcccagacac caaagttaat ttctatgcct      240
ggaagaggat ggaggtcggg cagcaggccg tagaagtctg gcagggcctg gccctgctgt      300
cggaagctgt cctgcgggc caggccctgt tggtcaactc ttcccagccg tgggagcccc       360
tgcagctgca tgtggataaa gccgtcagtg gccttcgcag cctcaccact ctgcttcggg      420
ctctgggagc cagaaggaa gccatctccc ctccagatgc ggcctcagct gctccactcc       480
gaacaatcac tgctgacact ttccgcaaac tcttccgagt ctactccaat ttcctccggg      540
gaaagctgaa gctgtacaca ggggaggcct gcaggacagg ggacagatga ccaggtgtgt      600
ccacctgggc atatccacca cctccctcac caacattgct tgtgccacac cctccccgc       660 cactcctgaa ccccgtcgag gggctctcag ctcagcgcca gcctgtccca tggacactcc      720
agtgccagca atgacatctc aggggccaga ggaactgtcc agagagcaac tctgagatct      780
aagaagcttg a                                                           791

<210> SEQ ID NO 4
<211> LENGTH: 193
<212> TYPE: PRT
<213> ORGANISM: Homo sapiens

<400> SEQUENCE: 4

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Ser Leu Phe Arg Val Tyr Ser Asn Phe Leu
                165                 170                 175

Arg Gly Lys Leu Lys Leu Tyr Thr Gly Glu Ala Cys Arg Thr Gly Asp
```

Arg

<210> SEQ ID NO 5
<211> LENGTH: 20
<212> TYPE: DNA
<213> ORGANISM: Artificial Sequence
<220> FEATURE:
<223> OTHER INFORMATION: Primer Hyg-Sfi, synthetic sequence

<400> SEQUENCE: 5
gaggccgcct cggcctctga                                            20

<210> SEQ ID NO 6
<211> LENGTH: 29
<212> TYPE: DNA
<213> ORGANISM: Artificial Sequence
<220> FEATURE:
<223> OTHER INFORMATION: Primer Hyg-BstX, synthetic sequence

<400> SEQUENCE: 6

2aaccatcgtg atgggtgcta ttcctttgc                                 29

<210> SEQ ID NO 7
<211> LENGTH: 20
<212> TYPE: DNA
<213> ORGANISM: Artificial Sequence
<220> FEATURE:
<223> OTHER INFORMATION: Primer HCG-A-F, synthetic sequence

<400> SEQUENCE: 7
atcctgcaaa aagcccagag                                            20

<210> SEQ ID NO 8
<211> LENGTH: 20
<212> TYPE: DNA
<213> ORGANISM: Artificial Sequence
<220> FEATURE:
<223> OTHER INFORMATION: Primer HCG-A-R, synthetic sequence

<400> SEQUENCE: 8
cttgaagcgt gtcaaagtgg                                            20

<210> SEQ ID NO 9
<211> LENGTH: 30
<212> TYPE: DNA
<213> ORGANISM: Artificial Sequence
<220> FEATURE:
<223> OTHER INFORMATION: Primer HCGA-ORF-F, synthetic sequence

<400> SEQUENCE: 9
gcgaattcgc caccatggat tactacagaa                                 30

<210> SEQ ID NO 10
<211> LENGTH: 25
<212> TYPE: DNA
<213> ORGANISM: Artificial Sequence
<220> FEATURE:
<223> OTHER INFORMATION: Primer HCGA-ORF-R, synthetic sequence

<400> SEQUENCE: 10
gcgaattctt aagatttgtg ataat                                      25

<210> SEQ ID NO 11
<211> LENGTH: 20

```
<212> TYPE: DNA
<213> ORGANISM: Artificial Sequence
<220> FEATURE:
<223> OTHER INFORMATION: Primer FSH-F, synthetic sequence

<400> SEQUENCE: 11
gaccacaggt gagtcttggc                                              20

<210> SEQ ID NO 12
<211> LENGTH: 20
<212> TYPE: DNA
<213> ORGANISM: Artificial Sequence
<220> FEATURE:
<223> OTHER INFORMATION: Primer FSH-R, synthetic sequence

<400> SEQUENCE: 12
tggtccttca ggacaagggt                                              20

<210> SEQ ID NO 13
<211> LENGTH: 30
<212> TYPE: DNA
<213> ORGANISM: Artificial Sequence
<220> FEATURE:
<223> OTHER INFORMATION: Primer FSH-F2, synthetic sequence

<400> SEQUENCE: 13
gcgaattcgc caccatgaag acactccagt                                   30

<210> SEQ ID NO 14
<211> LENGTH: 30
<212> TYPE: DNA
<213> ORGANISM: Artificial Sequence
<220> FEATURE:
<223> OTHER INFORMATION: Primer FSH-R2, synthetic sequence

<400> SEQUENCE: 14
taagaatgcg gccgcccact gatctttatt                                   30
```